United States Patent [19]

Gram et al.

[11] Patent Number: 4,843,888
[45] Date of Patent: Jul. 4, 1989

[54] SELF ALIGNING TEST GRIP

[75] Inventors: Martin M. Gram, St. Louis Park; Luther E. Johnson, St. Paul; Carl G. Larsen, Plymouth, all of Minn.

[73] Assignee: MTS Systems Corporation, Eden Prairie, Minn.

[21] Appl. No.: 176,932

[22] Filed: Apr. 4, 1988

Related U.S. Application Data

[63] Continuation-in-part of Ser. No. 77,598, Jul. 23, 1987, abandoned.

[51] Int. Cl.$^4$ .............................................. G01N 3/02
[52] U.S. Cl. ........................................ 73/856; 73/837
[58] Field of Search ................. 73/826, 831, 834, 837, 73/856, 808, 825, 856

[56] References Cited

U.S. PATENT DOCUMENTS

| | | | |
|---|---|---|---|
| 1,023,154 | 4/1912 | Kenerson | 73/862 |
| 1,865,070 | 6/1932 | Amsler | 73/860 |
| 3,320,798 | 5/1967 | Gram | 73/103 |
| 3,605,487 | 9/1971 | Corbett | 73/831 |
| 4,533,274 | 8/1985 | Moore | 403/31 |
| 4,686,860 | 8/1987 | Liu | 73/856 |

OTHER PUBLICATIONS

Lange, F. F. et al., Powder–Cushion Gripping ... Testing, Journal of Testing and Evaluation, vol. 6, No. 5, Sep. 1978, pp. 320–323.

Primary Examiner—Jerry W. Myracle
Attorney, Agent, or Firm—Kinney & Lange

[57] ABSTRACT

A tensile test grip for holding a specimen has a pullrod that is mounted in an annular bore, and carries a piston head that fits within a piston chamber, and both the pullrod and piston head are sealed on their outer surfaces with respect to the body forming the piston chamber, to form an enclosed chamber in which hydraulic fluid can be provided to permit swiveling alignment of the pullrod and the piston head relative to the housing that is a function of the direction of loading between the pullrod and the housing. The seal on the pullrod and the seal on the piston head with respect to the respective surfaces on which they seal is on a very short part spherical land to permit the pullrod and piston head to shift with respect to the housing and provide self alignment. The pullrod and piston can swivel freely for a limited amount to provide alignment during tensile loads. Spherical seats can be provided on the piston and arranged so that the seats can be locked together after initial alignment, to carry compression loads and permit testing the specimen in compression.

20 Claims, 3 Drawing Sheets

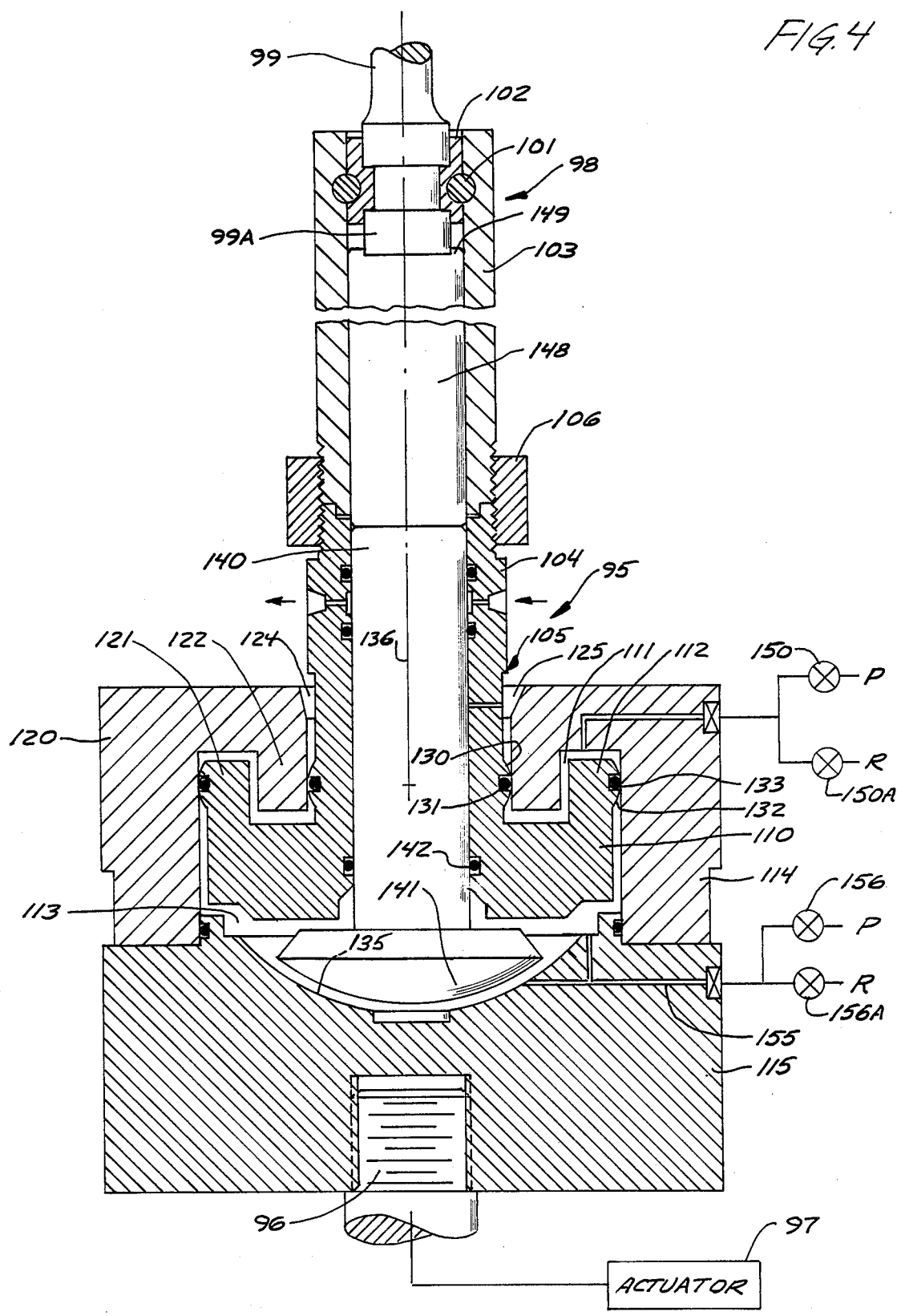

SELF ALIGNING TEST GRIP

CROSS REFERENCE TO RELATED APPLICATION

This application is a continuation in part of U.S. application Ser. No. 077,598, filed July 23, 1987 by Martin M. Gram, one of the inventors of this application, now abandoned.

BACKGROUND OF THE INVENTION

1. Field of the Invention.

The present invention relates to self-aligning grips for specimen testing machines.

2. Description of the Prior Art.

In the prior art, hydraulic cylinders that act in parallel to permit swiveling for alignment for testing machine grips are known. U.S. Pat. No. 1,865,070 shows pistons and cylinders that act in parallel with respect to a pullrod system for a tensile test, so that the force on the pullrods is equalized, and misalignment of the grip is minimized. The individual hydraulic cylinder and piston assemblies increase manufacturing costs, require a larger number of sealing surfaces, thus having a larger number of seals that are required, and in addition they provide more opportunity for binding.

Additionally, self aligning grips that use spherical seats are shown in U.S. Pat. No. 3,320,798 which uses a spherical seat cylinder for permitting alignment of the grip relative to the actuator rod, and then fluid pressure is used to lock the spherical seat parts in place with hydraulic pressure.

U. S. Pat. No. 1,023,154 to Kenerson shows a hydrostatic weighing machine, that uses a pressure that is measured for determining the weight being supported, and U.S. Pat. No. 4,533,274 to Moore shows a flexible joint that has annular elastomeric members arranged around a head that supports tension loads.

SUMMARY OF THE INVENTION

The present invention relates to a self aligning tensile grip utilizing a single annular piston arrangement that has a central pullrod connected to a specimen, and a piston head, which is mounted within a housing that is moved by an actuator of a tensile test machine. The piston reacts force to the specimen through a fluid that is supporting the load and which is confined with respect to the housing so it will flow to accommodate misalignment between the housing and the piston and pullrod.

In a preferred form the housing has a central sleeve, defining an annular interior surface. A chamber is formed between the sleeve and outer wall of the housing for receiving the piston head. The pullrod passes through the center of the sleeve, and the outer surface of the pullrod is sealed relative to the inner surface of the sleeve. The head also seals relative to the outer surface of the chamber in the preferred form. Both the pullrod and the piston head have seals that are on approximately the same plane and are supported in grooves formed in very short lands, or part spherical lands, to permit the pullrod and the head to swivel slightly relative to the housing to eliminate bending stresses on a specimen, such as a ceramic material specimen, held in a specimen grip attached to the pullrod. A small mechanical accumulator on the low pressure side of the piston can be used to accommodate variations in oil volume caused by temperature changes.

The arrangement is relatively easy to manufacture, and requires seals only on two surfaces, namely the interior of the sleeve, with report to the pullrod and the outer surface defining the chamber with report to the outer surface of the piston head. The alignment piston chamber substantially eliminates bending stresses on specimens.

In a modified form of the invention, the load is carried through a substantially noncompressible fluid that is enclosed within an annular bellows which defines a chamber supported by surfaces on the housing and on the piston head. Loads between the piston bead and housing will tend to compress the fluid. The bellows withstand radial pressures caused by loading, but the oil in the annular chamber formed around the pullrod will tend to flow within the bellows to permit self-alignment between the housing and the pullrod and piston head.

In a further modified form of the invention, a self-aligning piston and housing member for a grip are made so that they will carry both tension and compression loading. Compression loads are carried by aligning the parts forming the self-aligning members and then by forcing a spherical surface that moves with the self-aligning piston against a mating seat on the housing. The part-spherical surfaces are held under a load sufficient so that they will not shift during either tension or compression loading.

The self-aligning swivel, therefore, can be used with a grip for either tension or compression loading, making the grip adaptable to a wide variety of uses.

BRIEF DESCRIPTION OF THE DRAWINGS

FIG. 4 is a vertical sectional view of a self-aligning grip that is modified for use with both tension and compression loading, if desired, and operable for tension loading in the same manner as the previous forms of the invention.

DETAILED DESCRIPTION OF THE PREFERRED EMBODIMENTS

Figure 1:
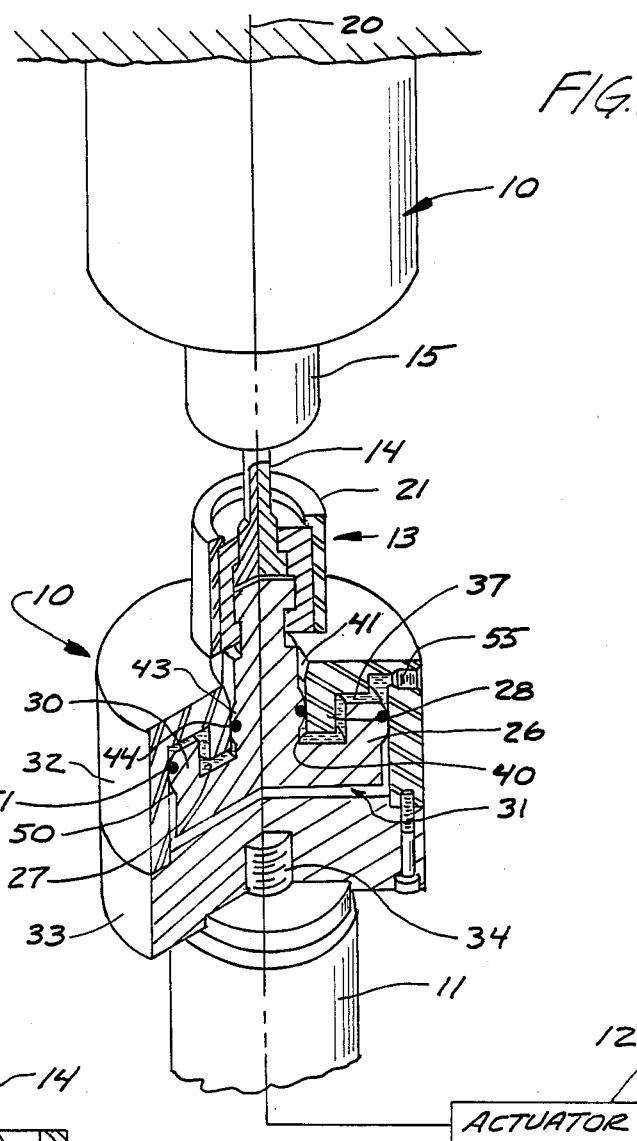
FIG. 1 is a perspective view of a specimen grip having a self alignment coupling made according to the present invention installed thereon.

A self aligning coupling or swivel assembly indicated generally at 10 is used for coupling an actuator rod 11 of an actuator 12, which is illustrated only schematically, to a grip member 13, which in turn is connected to a test specimen 14. The specimen 14 may be a ductile material or a brittle material such as a ceramic. A grip 15 grips the upper end of the specimen 14. Grip 15 is connected through a self aligning coupling or swivel assembly 10 to a load frame (not shown) through a load cell in a conventional manner. The apparatus shown is for applying tensile loads to specimen 14 along a central axis 20 that passes through the center of the specimen 14.

As shown, the grip 13 is a split collet grip that has an outer sleeve 21 acting to hold a collet 22 that is of precision manufacture, onto an end head 23 of a specimen. The collet 22 also engages and holds the collet connection head 24 of a grip pullrod 25. The grip pullrod 25 as shown has a piston head 26 fixed thereto. The piston head 26 has an annular groove 27 surrounding the pullrod 25, to form an outer annular rib 30. The piston head 26 is positioned within an interior cavity 31 that is formed in an enclosed housing 32. The housing has a base 33 that is coupled with a threaded screw 34 to the actuator rod 11, and has a cap 35 which defines an annular upper chamber 37 forming part of cavity 31, in which the annular rib 30 fits. The upper cap also has a central axial sleeve 28 formed therein positioned in the center of the cavity. The sleeve 28 has a central passageway 40 through which the pullrod 25 extends. The outermost portion 41 of the central passageway 40 of the sleeve is flared slightly, as shown.

The outer surface of the pullrod 25 has a land portion 43 that is slightly larger than the diameter of the main part of the pullrod, and the land portion 43 has a groove which has an annular seal 44 mounted therein. The land must be made so that it does not interfere with the bore of the housing when the piston rotates to accommodate misalignment, this can be accomplished by making the land spherical or very short for example. The seal 44 engages the inner surface 41 of the central passageway 40 of the sleeve 28, and provides a pressure seal to seal the interior tension loading chamber 37. The outer surface of the rib 30 forming the piston bead has a short (or spherical) land indicated generally at 50 that has a groove therein in which an annular seal 51 is mounted. The seal 51 seals against the outer annular surface defining the cavity 31 and chamber 37. The seal 51 divides the tension loading chamber 37 from a lower chamber 52 that is also a part of the cavity 31. The cavity 31 thus includes both chambers 37 and 52.

Hydraulic fluid is admitted into the upper tension loading chamber 37 through an inlet opening 55, which can be closed after filling the chamber to a desired volume when the self aligning coupling is to carry tension loads. The lower chamber 52 can also have a quantity of hydraulic fluid in it to prevent excessive movement when the specimen 14 breaks, or when there is a compression load.

Figure 2:
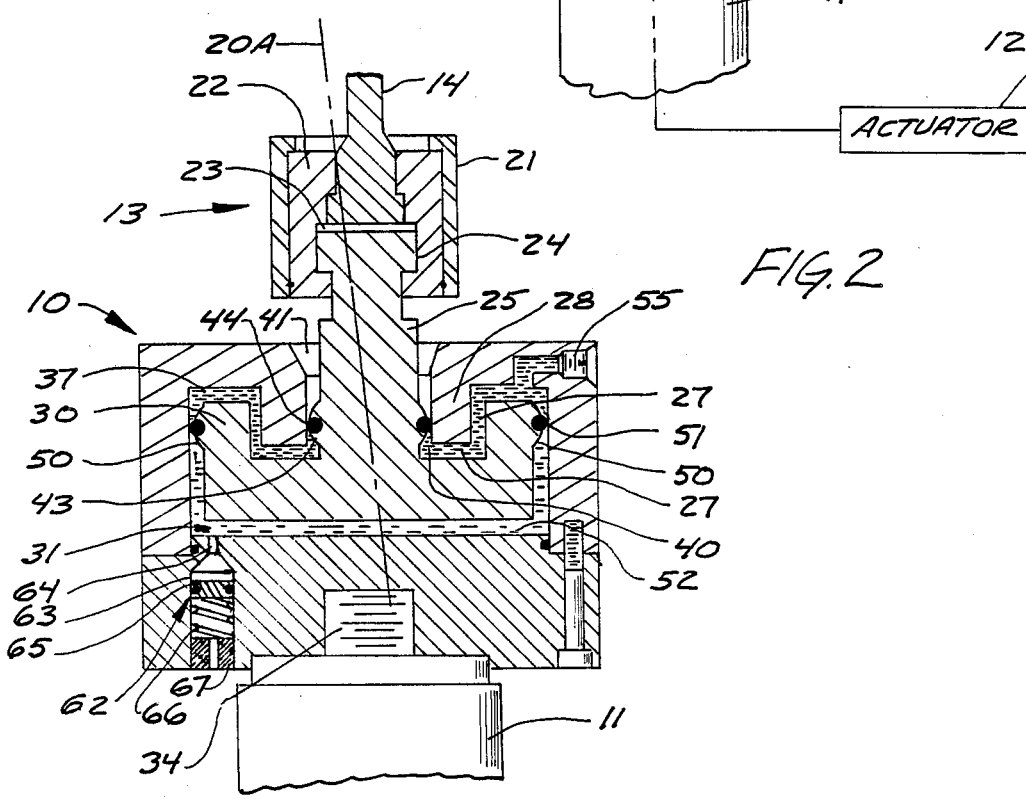
FIG. 2 is a vertical sectional view of the grip of FIG. 1.

It can be seen therefore that the piston head 26 and pullrod 25 can swivel as a unit slightly with respect to the housing, so that the central axis of the pullrod 25 can be slightly angularly offset from the central axis of the sleeve 28, without any substantial friction, other than the seals 44 and 51 rubbing against their sealing surfaces. This is shown in exaggerated form at 20A in FIG. 2. When a specimen 14 is placed into a grip attached to the self aligning coupling and the piston rod 11 is actuated initially, the pullrod 25, and piston head 26 can swivel to eliminate any bending loads on the specimen 14. Further, by "dithering" the actuator 12, under a slight tension load, the moment exerted by the friction on the seals is reduced so that the pullrod 25 and piston head 26 will tend to arrive at a position where there is substantially no bending loads on the specimen, and after which the tensile test load can be applied. The self aligning assembly 10 at the opposite end of the specimen will operate the same way as that explained for the lower assembly, to ensure that there is no bending moments introduced into the specimen 14 during the tensile test.

The unit is simple to make, having only one piston assembly, and provides for adequate swivelling to eliminate the bending loads that are detrimental in specimen testing.

Concentricity between the pullrod and the bores in which it operates, namely the sleeve surface 40 and the inner surface defining the cavity 31, is necessary for bending moment elimination. Very tight machining tolerances are required, but they are easy to obtain. The specimen end 23 must be closely controlled as to its concentricity, and the grip collet also must be closely controlled. The pullrod end head 24 also has to be precisely machined.

The planes of the seal grooves for seals 51 and 44 should be substantially coincident for eliminating any problems with inadequate swiveling. The sleeve surfaces 40 and the outer surface of the cavity 31 should be concentric.

The pullrod 25 is guided axially by a short or spherical land which acts as a piston, on a smooth bore which can be precisely machined and eliminates a good deal of friction. The swivel action is made possible by short coplanar piston lands, which can swivel, and thus gives quite precise operation.

The pullrod and housing swivel assembly can be used with other types of specimen attaching grips as well as the collet type grips disclosed herein.

The lower chamber 31 is preferably filled with non-compressible fluid to absorb the shocks that occur when a specimen breaks. The volume of oil can be controlled with valves to center the piston in the housing for use, (as shown in FIG. 4). Problems can arise with temperature changes to create either a vacuum or excess pressure in the chamber 31. Increases in pressure cause increased seal friction, which may tend to eccentrically load a brittle ceramic specimen. If a vacuum is created in the chamber 31, air might be introduced, and this would reduce the stiffness of the load path.

To overcome these problems, a mechanical accumulator indicated generally at 62 is formed in a passageway or bore 63 that is formed in the housing. An orifice 64 connects bore 63 and the chamber 31. The bore 63 mounts a suitable plunger or piston 65 that is backed with a spring 66, and the spring 66 tends to urge the piston toward the chamber 31 with a light force to a neutral position. The spring 66 is held in place in the bore 63 with a suitable vented plug 67. The spring 66 will urge the plunger or piston 65 toward the orifice 64 and will provide an accumulator effect to maintain a stable pressure level in the chamber 31 within a reasonable range of oil volume changes and under shock loads from breaking specimens. If the oil in chamber 31 tends to expand, it will cause the piston 65 to move against the urging of the spring 66 to accomodate the volume change, which gives an accumulator effect. The oil then can flow into the bore 63 if temperature rises and out of the bore if temperature decreases. Excessive pressures or vacuum will not be created in chamber 31.

The volume in the bore 63 is such that if the oil tends to contract because of temperature changes, some makeup oil can be provided by the accumulator to avoid a vacuum being created. The mechanical accumulator, of course, can be varied in size and more than one small accumulator can be placed in the housing.

Figure 3:
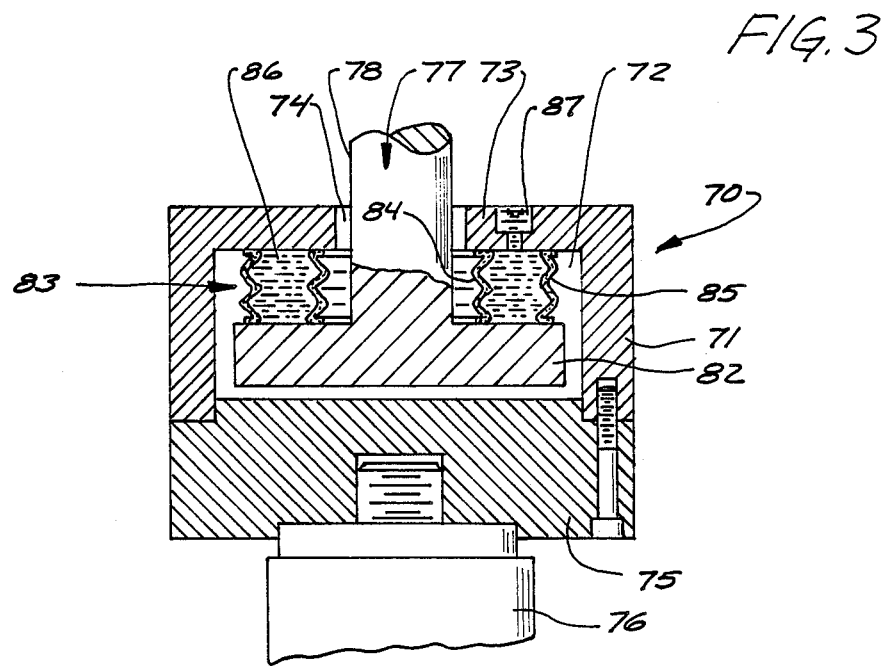
FIG. 3 is a vertical sectional view of a modified form of the invention utilizing a single chamber formed with a bellows having a filling of hydraulic oil for supporting tension loads between a piston head and a housing.

In FIG. 3, a modified form of the invention is shown which self-aligns under tension loading using an annular piston and cylinder, but in this form of the invention, the schematic showing illustrates a self-aligning mounting for a specimen grip indicated generally at 70, which includes an outer housing 71 constructed to have an interior chamber 72, and an end wall 73 with a bore 74 therein. The housing has a base 75 that has an actuator rod 76 connected thereto.

A pullrod assembly 77 includes a pullrod 78 which passes through the opening or bore 74, and which has a head 82 integral therewith and positioned within the chamber 72. Of course, the chamber end wall 73 can be made so that it is removable for installation, by having suitable cap screws to hold it on to the sidewalls of the housing 71.

In order to obtain load carrying capability and self-aligning capabilities under tension loading on the pullrod, an annular bellows assembly 83 is utilized in this form of the invention. The bellows assembly 83 includes an inner bellows wall 84, and an outer bellows wall 85 which are both annular and are concentric. The walls S4 and 85 extend around the central pullrod 78 to define an annular chamber 86 which is filled with a substantially noncompressible fluid (hydraulic oil) through a suitable fill port 87 which as shown has a plug in it for keeping the oil in place.

The bellows walls 84 and 85 are suitably attached, such as with seam welding, to the undersurface of the top wall 73 of the housing and to the surface of the head 82 facing wall 73 to form the enclosed or sealed chamber 86.

The loads then are carried through the fluid which will be under pressure, but which will flow within the chamber 86 sufficiently to accommodate misalignment between the axis of the actuator rod and pullrod to avoid excessive bending on the specimen. The radial strength of the bellows is such that the bellows will not bulge out excessively during the loading, and the self-aligning features can be obtained with a chamber that acts as a piston would, inside an outer housing, to support the head 82 on the substantially noncompressible fluid which is trapped within the chamber 86.

Referring specifically to FIG. 4, a form of the invention which permits loading in both tension and compression is illustrated. The swivel utilizes substantially the same tension load carrying piston arrangement as that shown in FIGS. 1 and 2, but the outer housing has a spherical concave seat formed in the bottom surface of the lower chamber, which is made to support a spherical convex surface on a self-aligning piston. For compression loading the piston is pressurized to lock the spherical seats tightly together. The locking is carried out after applying a tension load to self-align the piston and pullrod.

As shown, a self-aligning tension and compression carrying swivel assembly indicated generally at 95 is used for coupling an actuator rod shown fragmentarily at 96, operated by an actuator 97, which is illustrated schematically, to a collet type grip member indicated generally at 98. The grip member 98 retains a specimen 99 that is to loaded. The specimen 99, in this form of the invention, is one which is to be loaded in compression, and also tension if desired. A suitable grip is attached to the upper end of the specimen 99, and connected to a load frame in a conventional manner through a separate self-aligning swivel assembly. The specimen 99 is held in a collet indicated generally at 102 that fits within a load sleeve 103. A pair of pins 101 that fit partially in a groove on the outside of the collet as shown and partially in the load sleeve can be used. The load sleeve 103 is coupled with a coupling 106 to a tubular pullrod 104 of the piston assembly 105. The pullrod 104 is used for tension loading of a specimen. Coupling 106 is made so that the parts can be held under compressive load, that is the ends of the load sleeve 103 and the pullrod 104 are abutting under a preload.

The pullrod 104 is integrally made with a cup type piston head 110, that is formed with an annular groove 111 surrounding the pullrod 104 to form an annular outer rim or rib 112. The piston head 110 is positioned within an interior cavity 113 that is formed in an enclosed housing 114. The housing 114 has a base member 115 that is coupled to and moves with the actuator rod 96. A cap member 120 is suitably fastened to the base 115 with cap screws and has an annular chamber portion 121 in which the annular rib or rim 112 of the piston head fits. The cap 120 has a passage interior sleeve 122 formed therein which forms a central passageway 124 and which surrounds the pullrod 104. The outermost portion of the passageway 124 is flared slightly as shown at 125, for permitting some angular movement of the pullrod relative to the housing.

Pullrod 104 has a part spherical land indicated at 130 thereon in which a groove is formed to mount an 0-ring 131 that seals on the surface defining the passageway 124. The outer rim 112 of the piston head 110 has a part spherical land indicated at 132, which has a groove in it for providing a mounting for an O-ring 133 to seal on the interior surface of the chamber 113. The "O" rings 131 and 133 are on a common plane perpendicular to a central axis 136 of the pullrod 104.

The base portion 115 of the housing has an interior end surface formed as a part spherical concave surface 135 that is generated substantially about a center coinciding with the intersection between the central axis 136 of the pullrod 104 and the plane bisecting 0-rings 131 and 133. The center point is the center of swivel for the pullrod and piston head 110 relative to the housing 114. In other words, the part spherical concave surface 135 is generated about the axis 136.

The pullrod 104 connected to the piston head 110 is tubular, and a shaft 140 is mounted therein. The shaft 140 has a head 141 that has a part spherical convex end surface which mates with the surface 135. The shaft 140 is sealed with respect to the chamber 113 utilizing an 0-ring seal 142 on the interior bore through the pullrod 104, near the end where the head 110 is formed.

Shaft 140 is abutted against a control shaft 148 that in turn has a pilot receptacle 149 for receiving an end portion 99A of the specimen 99.

The loading path for tension is from the actuator shaft 96 through the housing 114, and through the fluid under pressure in the chamber 111, which is controlled from a pressure source through a valve 150, so that a suitable amount of fluid under pressure is supplied within chamber 111. Load on the actuator then will be transmitted through this fluid under pressure, to the piston head and to the pullrod 104, and then through the load sleeve 103, through the retainer pins 101 and through the split collet 102 to the specimen 99. The self-alignment in the tension mode, when the actuator rod is exerting a tension load on the specimen 99 is exactly as was described in the first form of the invention and the fluid in the chamber 111 will shift, to accommodate misalignments between the axis of the housing, and thus the axis of the actuator rod 96, and the axis of the specimen, to remove any side loading.

The load sleeve 103 is made so that the pullrod can be sectioned and the end adjacent the specimen can be made of high temperature resistant materials when the ceramic specimen 99 is being tested under high temperatures.

In order to control the position of the piston 110, the chamber 113 is connected through a passageway 155 to a source of pressure through a valve 156, and is connected to a drain valve 156A, so that fluid under pressure can be added or removed from chamber 113.

If the specimen is to be loaded in compression, or alternating compression and tension, the valves 150, 150A and 156A are used to center the piston head 110 in its chamber. Then the control shaft 14B is pushed downwardly in the load sleeve 103 so that the specimen 99 can be inserted, and the pins 101 used in the collet 102 to hold the specimen in place. A low level tension load is put on the specimen through the actuator 97, to seat the specimen in the collet and take up slack.

Then, the valve 156A is opened so that pressure can be relieved from the chamber 113, and pressure is provided to the chamber 111 through the valve 150 to slowly move the piston 110, and through the pullrod 104 the load sleeve 103. The end of the specimen will abut on the control shaft 148, moving the shaft 140 and the head 141 toward the surface 135 until the part spherical surface 141A bottoms out on the spherical surface 135. The pressure on the tension side of the piston head 110, that is, in chamber 111, will go to line pressure forcing together the two part-spherical surfaces under a substantial force. Using two self-aligning grips, one on each end of the specimen, will require repeating the operation to seat the spherical head 141 against the seat 135 on the second grip.

Then the self-aligning grips are fully preloaded to a level defined by the pressure from the pressure source through valve 150 times the area of the piston head 110. The pressure provides a locking force holding the head 141 and the spherical seat 135 together. Friction holds the surfaces to prevent the pull rod from changing in alignment with load. Compression loads are carried through the surfaces 135 and 141A to shaft 140 which bears on control shaft 148. The shaft 148 abuts on the specimen to load it in compression. In this way, self-aligning is obtained for the compression loading by first applying the tension load to align the pullrod and housing with the specimen, and then seating the spherical surfaces under adequate force.

Although the present invention has been described with reference to preferred embodiments, workers skilled in the art will recognize that changes may be made in form and detail without departing from the spirit and scope of the invention.

What is claimed is:

1. A self aligning swivel for use in a testing machine having means for applying a load to a specimen comprising:
    an outer housing;
    means for coupling said outer housing to a first member for loading by a testing machine;
    a pullrod assembly mounted in said outer housing including a central pullrod, and a piston head member, said outer housing having a cavity formed therein in which the piston head member fits, and a wall portion overlying the piston head member and having a central passageway through which the central pullrod passes;
    means carried by the pullrod assembly for defining an enclosed annular chamber surrounding the central pullrod between the piston head member and the housing on a side of the piston head member facing in direction of the central pullrod and being oriented to permit swivelling movement of the axis of the central pullrod with respect to the outer housing; and
    a filling of hydraulic fluid in the enclosed chamber so the hydraulic fluid supports loads applied on the central pullrod in a first direction and reacted through the means for loading when the self-aligning swivel is mounted in a testing machine.

2. The apparatus as specified in claim 1 wherein said central passageway forms a sleeve member encircling the pullrod, and wherein said piston head has a rib that fits between said sleeve member and an outer surface defining said cavity formed in said housing, said annular chamber being formed by seal means between the piston head member and the outer surface defining the cavity, and separate seal means between the central pullrod and the sleeve member, the seal means being carried by lands on the outer surface of the piston head member and the central pullrod respectively.

3. The apparatus as specified in claim 2 and a filling of hydraulic fluid in cavity on an opposite side of the seal means from the first mentioned filling of hydraulic fluid, and accumulator means open to the cavity at the opposite side of the seal means from the first mentioned filing of hydraulic fluid.

4. The apparatus as specified in claim 1 wherein said lands comprise convex part spherical surfaces in the region of said seal means on both the central pullrod and the piston head member.

5. The apparatus as specified in claim 1 wherein said housing has means to attach an actuator rod thereto, and said pullrod member has means thereon for coupling to a specimen to be tested.

6. The apparatus of claim 1 wherein the means defining the enclosed chamber comprises a pair of annular substantially concentric flexible walls which are spaced apart and which walls are sealed with respect to a surface of the piston head member and the wall portion of the housing overlying the piston head member.

7. The self-aligning swivel as claimed in claim 1 wherein said central pullrod and piston head have a central bore therethrough, centered on a longitudinal axis of the central pullrod; means for coupling a load carrying member to the central pullrod, and means carried in the bore for compressively engaging the means coupled to the central pullrod for loading, said means carried in the bore including a shaft member protruding from the piston head on the interior of the cavity on a side of the piston head member opposite from the annular chamber, said shaft having a second head thereon which has an outwardly facing convex substantially part spherical surface, interior cavity of said housing having a base surface that is complimentary in shape to the part spherical surface of the head member, and means to control the position of the piston head member to cause the piston head member to be moved and carry loads through the central pullrod, the means for attaching the load carrying member, and through the compressive carrying member to urge the outwardly facing surface of the second head member against the base surface of the cavity as a function of the pressure in the first mentioned annular chamber, and means to regulate the pressure in the annular chamber to control the force with which the base surface of the cavity and the outwardly facing surface of the second head member engage.

8. The apparatus of claim 1 and an annular piston head member surrounding the pullrod, the piston head member slidably fitting into the cavity, a central passageway leading from the cavity through the housing, the pullrod passing through the central passageway to the exterior of the housing, the pullrod having a longitudinal axis;

land means formed on the outer surfaces of each of the pullrod and the piston head member, each land means having groove means defined therein for mounting annular seals in each of said land means, said seals sealing on the outer surface defining the cavity and on the surface defining the central passageway, respectively, said land means being oriented to permit angular movement of the longitudinal axis of the pullrod with respect to the housing while maintaining a seal with the seals on both of the land means; and the filling of hydraulic fluid being in a chamber formed by the seals.

9. A self aligning swivel for use with a testing machine having first load application means and second load reaction means, said swivel comprising:

an outer housing;

means for coupling said outer housing to one of the first and second means of a testing machine;

a pullrod assembly mounted in said outer housing including a central pullrod adapted to be coupled to the other of the first and second means of a testing machine, and a piston head member, said outer housing having a cavity formed therein in which the piston head member fits, and a central wall portion overlying the piston head member, the central wall portion having a central passageway through which the central pullrod passes;

land means formed on the outer surfaces of each of the central pullrod and the piston head member, at substantially the same lateral plane, each land means having groove means defined therein for mounting annular seals in each of said land means, the seals sealing on the surface of the housing defining the outer surface of the cavity and on the surface defining the central passageway, respectively, said land means being oriented to permit swivelling movement between the housing and the central pullrod; and a filling of hydraulic fluid on a portion of the cavity sealed by the seals on a side of the seals so the hydraulic fluid supports loads applied between the central pullrod and the housing by the first and second means of a testing machine in which the swivel member is used when the load is in a direction tending to compress the hydraulic fluid.

10. The apparatus as specified in claim 9 wherein said central wall portion forms a sleeve member encircling the central pullrod, and wherein said piston head member has a rib that fits between said sleeve member and the outer surface of said cavity.

11. The apparatus of claim 10 wherein the plane of the land means is substantially perpendicular to a longitudinal axis of the central pullrod.

12. The apparatus as specified in claim 9 wherein said land means comprises convex part spherical surfaces in the region of said seal means.

13. The apparatus as specified in claim 9 wherein said housing has means to attach an actuator rod thereto which comprises the first means, and said pullrod member has means therein for coupling to a specimen to be tested, which in turn is coupled to the second means.

14. The apparatus as specified in claim 9 and a filling of hydraulic fluid in the cavity on an opposite side of the seal means from the first mentioned filling of hydraulic fluid.

15. The self-aligning swivel as claimed in claim 9 wherein said pullrod and piston head member have a central bore therethrough, centered on a longitudinal axis of the central pullrod; and means for coupling a load carrying member to the central pullrod, and means carried in the central bore for compressively engaging the means coupled to the central pullrod for loading, said means carried in the bore including a shaft member protruding from the piston head member on the interior of the cavity on a side of the piston head member opposite from the annular chamber, said shaft having a second head member thereon which has an outwardly facing substantially part spherical surface, the interior cavity of said housing having a base surface that is complimentary in shape to the part spherical surface of the second head member, and means for controlling the position of the piston head member to cause the piston head member to move against the second head member to urge the outwardly facing surface of the second head member against the base surface of the cavity, as a function of the pressure in the first mentioned annular chamber, and means for regulating the pressure in the annular chamber to control the force with which the base surface of the cavity and the outwardly facing surface of the second head member engage.

16. A self aligning assembly for coupling to a specimen grip a testing machine comprising;

an outer housing having an interior cavity;

means for coupling said outer housing to a first member of a testing machine;

a pullrod assembly mounted in said cavity and including a central pullrod, and an annular piston head member surrounding the pullrod, the piston head member slidably fitting into the cavity, a central passageway leading from the cavity through the housing, the central pullrod passing through the central passageway to the exterior of the housing, the central pullrod having a longitudinal axis;

land means formed on the outer surfaces of each of the central pullrod and the piston head member, each land means having groove means defined therein for mounting annular seals in each of said land means, said seals sealing on the outer surface defining the cavity and on the surface defining the central passageway, respectively, said land means being oriented to permit angular movement of the longitudinal axis of the central pullrod with respect to the housing while maintaining a seal with the seals on both of the land means; and a filling of hydraulic fluid on a portion of the cavity formed into a load carrying chamber by the annular seals.

17. The assembly of claim 16 wherein the land means comprises annular convex part spherical surfaces.

18. The assembly of claim 17, wherein said central passageway is defined in part with a sleeve extending into the cavity, the piston head member having a rib thereon overlapping a portion of the sleeve within the cavity, and the land means on the piston head member and the central pullrod being on substantially the same plane.

19. The assembly of claim 17 wherein a second chamber is formed in the cavity on the opposite side of the annular seals from the load carrying chamber, a filling of hydraulic fluid in the second chamber, and accumulator means open to the second chamber.

20. The assembly of claim 19 wherein said accumulator means comprises a bore in the outer housing open to the second chamber, and spring loaded piston means in the bore that moves as a function of pressure in the second chamber.

* * * * *